United States Patent
Moriguchi

(10) Patent No.: US 10,765,317 B2
(45) Date of Patent: Sep. 8, 2020

(54) OPHTHALMOLOGICAL IMAGING DEVICE

(71) Applicant: TOPCON CORPORATION, Itabashi-ku, Tokyo (JP)

(72) Inventor: Yoshikiyo Moriguchi, Sendai (JP)

(73) Assignee: TOPCON CORPORATION, Itabashi-ku, Tokyo (JP)

( * ) Notice: Subject to any disclaimer, the term of this patent is extended or adjusted under 35 U.S.C. 154(b) by 0 days.

(21) Appl. No.: 15/771,459

(22) PCT Filed: Oct. 19, 2016

(86) PCT No.: PCT/JP2016/080887
§ 371 (c)(1),
(2) Date: Apr. 27, 2018

(87) PCT Pub. No.: WO2017/073413
PCT Pub. Date: May 4, 2017

(65) Prior Publication Data
US 2018/0303339 A1 Oct. 25, 2018

(30) Foreign Application Priority Data

Oct. 29, 2015 (JP) .................................. 2015-212805

(51) Int. Cl.
*A61B 3/15* (2006.01)
*A61B 3/10* (2006.01)
(Continued)

(52) U.S. Cl.
CPC ............ *A61B 3/152* (2013.01); *A61B 3/0008* (2013.01); *A61B 3/0083* (2013.01); *A61B 3/10* (2013.01);
(Continued)

(58) Field of Classification Search
None
See application file for complete search history.

(56) References Cited

U.S. PATENT DOCUMENTS 7,527,378 B2    5/2009  Fukuma et al.
2007/0188765 A1 8/2007  Zhao et al.
(Continued)

FOREIGN PATENT DOCUMENTS

JP    2009-523564 A    6/2009
JP    2012-213617 A    11/2012
JP    2016-075585 A    5/2016

OTHER PUBLICATIONS

International Search Report dated Dec. 13, 2016, in connection with International Patent Application No. PCT/JP2016/080887, 3 pgs.
(Continued)

Primary Examiner — Darryl J Collins
Assistant Examiner — Journey F Sumlar
(74) Attorney, Agent, or Firm — Chiesa Shahinian & Giantomasi PC

(57) ABSTRACT

An ophthalmological imaging device comprising an objective lens, an interference optical system, an image forming unit, an optical member, and an analyzer. The interference optical system divides light from a light source into measurement light and reference light, causes the measurement light to become incident on a subject's eye via the objective lens, and detects interference light between the reference light and return light of the measurement light that has exited from the subject's eye and passed through the objective lens. The image forming unit forms an image of the subject's eye based on a detection result of the interference light which are acquired by the interference optical system. The analyzer analyzes a first detection result and a second detection result of the interference light to eliminate noise in the second detection result or in an image based on the second detection result.

10 Claims, 8 Drawing Sheets

(51) Int. Cl.
   *A61B 3/00* (2006.01)
   *A61B 3/12* (2006.01)
(52) U.S. Cl.
   CPC ............... *A61B 3/102* (2013.01); *A61B 3/12* (2013.01); *A61B 3/0025* (2013.01); *A61B 2576/02* (2013.01)

(56) References Cited

U.S. PATENT DOCUMENTS

| | | |
|---|---|---|
| 2012/0250029 A1 | 10/2012 | Yoshida |
| 2013/0094339 A1* | 4/2013 | Aiba ...................... G11B 20/18 369/53.35 |
| 2014/0029015 A1 | 1/2014 | Schmoll et al. |
| 2015/0342459 A1* | 12/2015 | Robert ................. A61B 3/0033 351/205 |
| 2016/0097632 A1 | 4/2016 | Sumiya et al. |

OTHER PUBLICATIONS

Extended European Search Report dated Jun. 4, 2019, in connection with European Patent Application No. 16859643.5, 7 pgs.
Notice of Reasons for Refusal dated Jul. 23, 2019, in connection with Japanese Patent Application No. 2015-212805, 4 pgs.

\* cited by examiner

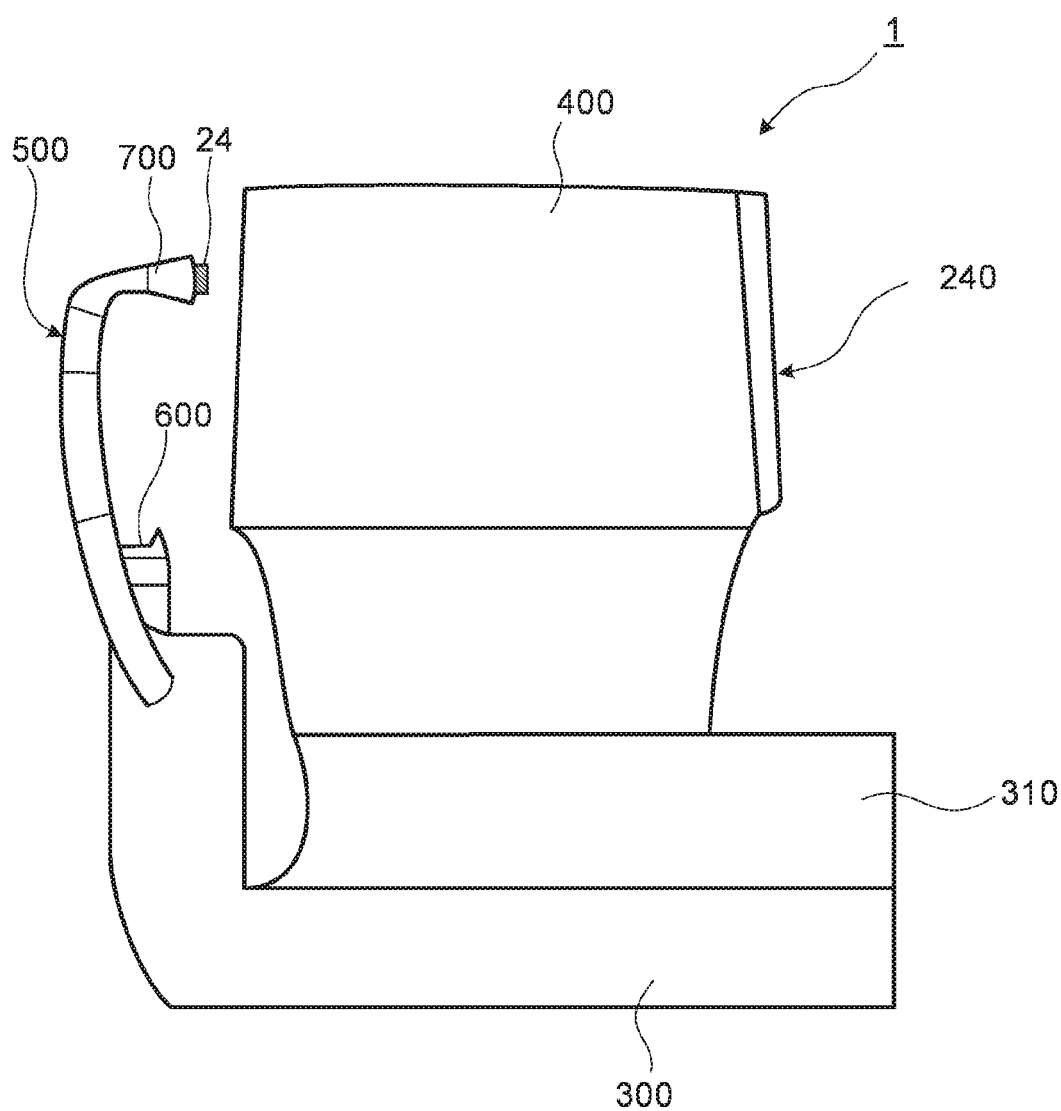

OPHTHALMOLOGICAL IMAGING DEVICE

CROSS-REFERENCE TO RELATED APPLICATIONS

This application is a national stage (under 35 U.S.C. 371) of International Patent Application No. PCT/JP2016/080887, filed Oct. 19, 2016, claiming priority to Japanese Patent Application No. 2015-212805, filed Oct. 29, 2015, both of which are herein incorporated by reference in their entirety.

FIELD

The present invention relates to an ophthalmological imaging device.

BACKGROUND

An optical coherence tomography (OCT, hereafter) is used for forming images representing a surface morphology and an internal morphology of an object to be measured. An artifact due to a reflection from an object other than the object to be measured or a phenomenon of coherence revival may appear in an OCT image acquired by using OCT. Their artifacts may appear overlapping with the attention site or affect results of image processing such as a segmentation processing, or the like.

For example, an artifact due to a reflection from the object other than the object to be measured may be removed by applying an anti-reflection coating to an optical member constituting an interference optical system for acquiring the OCT image. Also, a method to remove an artifact by performing phase modulation with respect to light from a light source so as to suppress occurrence of the phenomenon of coherence revival is known (US Unexamined Patent Application Publication No. 2014/0029015).

However, even if the anti-reflection coating is applied to the optical member, it is difficult to suppress the reflection perfectly. In addition, in the method disclosed in US Unexamined Patent Application Publication No. 2014/0029015, design depending on an optical condition such as kinds or placement of the optical member constituting the optical system is needed, and thereby this makes it complicated to design the optical system and a control system.

In general, artifacts due to the reflection from the object other than the object to be measured are more likely to appear in the OCT image as coherence length becomes longer. Furthermore, artifacts due to the phenomenon of coherence revival are more likely to appear in the OCT image as interval of coherence revival becomes shorter. Therefore, in case of using a light source of which coherence length is long or a light source of which interval of coherence revival is short, deterioration of the OCT image is more likely to occur, and thereby a new technology is required to remove the artifact described above.

SUMMARY OF THE EMBODIMENTS

The present invention is made to solve the aforementioned problem, and the object thereof is to provide a novel technology for removing artifacts appeared in an image acquired by using an interference optical system.

An ophthalmological imaging device according to the embodiments comprises an objective lens, an interference optical system, an image forming unit, an optical member, and an analyzer. The interference optical system divides light from a light source into measurement light and reference light, causes the measurement light to become incident on a subject's eye via the objective lens, and detects interference light between the reference light and return light of the measurement light that has exited from the subject's eye and passed through the objective lens. The image forming unit forms an image of the subject's eye based on a detection result of the interference light which are acquired by the interference optical system. The optical member is capable of being disposed in an optical path of the measurement light, and absorbs the measurement light. The analyzer analyzes a first detection result of the interference light which are acquired by the interference optical system while the optical member is in of being disposed in the optical path, and a second detection result of the interference light which are acquired by interference optical system while the optical member is in a state of having been removed from the optical path, to eliminate noise in the second detection result or in an image based on the second detection result.

According to the embodiments, a novel technology for removing artifacts appeared in an image acquired by using an interference optical system can be provided.

BRIEF DESCRIPTION OF THE DRAWINGS

FIG. 8 is a schematic diagram illustrating a principal part of the configuration of an ophthalmological imaging device according to a sixth modification example of the embodiments.

DETAILED DESCRIPTION OF THE EMBODIMENTS

Figure 1:
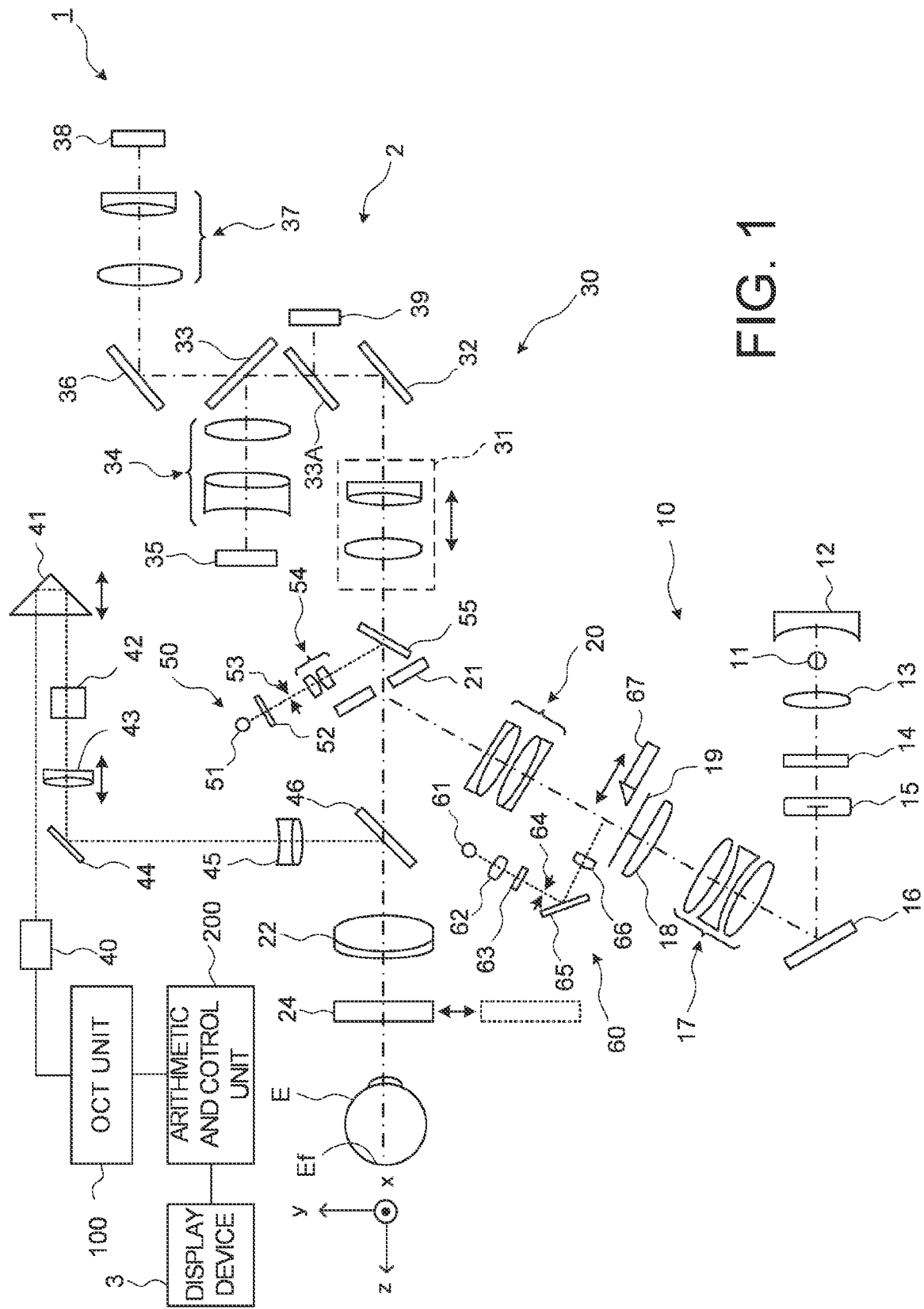
FIG. 1 is a schematic diagram illustrating an example of the configuration of an ophthalmological imaging device according embodiments.

Exemplary embodiments of the present invention will be described in detail with referring to the drawings. An ophthalmological imaging device according to the present invention has a function of an optical coherence tomography apparatus and performs optical coherence tomography on a subject's eye. The OCT is performed on an arbitrary site of the subject's eye, for example, on the fundus or on the anterior segment.

In this specification, images acquired by OCT may be collectively referred to as OCT images. Further, in some cases in the following description, noise and artifacts may be treated in the same way and represented noise as artifacts. In addition, the contents of the documents cited in the specification can be incorporated as contents of the following embodiments.

The following embodiments describe an ophthalmological imaging device capable of performing Fourier-domain-type OCT. In particular, the method of swept-source-type OCT can be applied to the ophthalmological imaging device according to the embodiments. It should be noted that the configuration according to the present embodiments can also be applied to an ophthalmological imaging device capable of performing OCT of other type than the swept-source-type OCT such as spectral domain OCT. In addition, the following embodiments describe an apparatus in which an OCT apparatus and a fundus camera are combined. However, it is also possible to combine an OCT apparatus that has the configuration according to the embodiments with a modality other than the fundus camera, for example, a scanning laser ophthalmoscope (SLO), a slit lamp microscope, an ophthalmic surgical microscope, a photocoagulation apparatus, or the like. Alternatively, the configuration of the embodiments may be applied to a single-functional OCT device.

[Configuration]

As shown in FIG. 1, the ophthalmological imaging device 1 includes a fundus camera unit 2, an OCT unit 100, and an arithmetic and control unit 200. The fundus camera unit 2 has substantially the same optical system as the conventional fundus camera. The OCT unit 100 is provided with an optical system for performing OCT. The arithmetic and control unit 200 is provided with a computer for performing various arithmetic processes and control processes.

[Fundus Camera Unit]

The fundus camera unit 2 illustrated in FIG. 1 is provided with an optical system for acquiring two dimensional images (fundus images) rendering the surface morphology of a fundus Ef of a subject's eye E. Examples of the fundus images include observation images and photographed images. An observation image is, for example, a monochrome moving image formed at a predetermined frame rate using near-infrared light. A photographed image may be, for example, a color image captured by flashing visible light, or a monochrome still image using near-infrared light or visible light as illumination light. The fundus camera unit 2 may be configured to be capable of acquiring other types of images such as fluorescein angiograms, indocyanine green angiograms, and autofluorescent angiograms.

The fundus camera unit 2 is provided with a jaw holder and a forehead rest for supporting the face of the subject. Further, the fundus camera unit 2 is provided with an illumination optical system 10 and an imaging optical system 30. The illumination optical system 10 projects illumination light onto the fundus Ef. The imaging optical system 30 guides the illumination light reflected from the fundus to imaging devices (CCD image sensors 35 and 38, sometimes simply referred to as "CCD"). Further, the imaging optical system 30 guides measurement light coming from the OCT unit 100 to the subject's eye E, and guides the measurement light returning from the subject's eye E to the OCT unit 100.

An observation light source 11 of the illumination optical system 10 includes, for example, a halogen lamp or a light emitting diode (LED). Light (observation illumination light) emitted from the observation light source 11 is reflected by a reflection mirror 12 having a curved reflective surface, and becomes near-infrared light after penetrating a visible cut filter 14 via a condenser lens 13. Further, the observation illumination light is once converged near an imaging light source 15, reflected by a mirror 16, and passes through relay lenses 17 and 18, a diaphragm 19, and a relay lens 20. Then, the observation illumination light is reflected on the peripheral part (the surrounding area of an aperture part) of an aperture mirror 21, penetrates a dichroic mirror 46, and is guided to an objective lens 22.

A shutter 24 is inserted into and removed from an optical path between the objective lens 22 and the subject's eye E. The shutter 24 shields light which passes through the objective lens 22 and heads toward the subject's eye E, as a shielding member. In addition, the shutter 24 absorbs the light heading toward the subject's eye E and suppresses a reflection by the shutter 24. A absorbing member may be provided on a surface of the shutter 24 on the objective lens 22 side so as to include an illuminating area of the light heading toward the subject's eye E. The shutter 24 like this serves as a protective member for the objective lens 22 for preventing lens surface from an adhesion of dirt and a formation of scratches and for preventing from an entry of dust and the like. The shutter 24 may absorb at least measurement light guided from the OCT unit 100 to the objective lens 22, but it may absorb light other than the measurement light passing through the objective lens 22. The shutter 24 is inserted into an optical path of the measurement light in the case of acquiring reference data described after, and the shutter 24 is removed from the optical path of the measurement light in other cases. Hereinafter, it is assumed that the shutter 24 is removed from the optical path of the measurement light unless otherwise mentioned.

In case that the shutter 24 has been removed from the optical path of the measurement light, the observation illumination light guided to the objective lens 22 is refracted by the objective lens 22 and illuminates the fundus Ef. The observation illumination light reflected from the fundus is refracted by the objective lens 22, penetrates the dichroic mirror 46, passes through the aperture part formed in the center area of the aperture mirror 21, penetrates a dichroic mirror 55, travels through a focusing lens 31, and is reflected by a mirror 32. Further, the fundus reflection light penetrates a half mirror 33A, is reflected by a dichroic mirror 33, and forms an image on the light receiving surface of the CCD image sensor 35 by a condenser lens 34. The CCD image sensor 35 detects the fundus reflection light at a predetermined frame rate, for example. An image (observation image) based on the fundus reflection light detected by the CCD image sensor 35 is displayed on a display device 3. Note that when the imaging optical system 30 is focused on the anterior segment, an observation image of the anterior segment of the subject's eye E is displayed.

The imaging light source 15 is formed of, for example, a xenon lamp or an LED. The light (imaging illumination light) output from the imaging light source 15 is projected onto the fundus Ef via the same route as that of the observation illumination light. The fundus reflection light of the imaging illumination light is guided to the dichroic mirror 33 via the same route as that of the observation illumination light, penetrates the dichroic mirror 33, is reflected by a mirror 36, and forms an image on the light receiving surface of the CCD image sensor 38 by a condenser lens 37. The display device 3 displays an image (photographed image) based on the fundus reflection light detected by the CCD image sensor 38. Note that the same device or different devices may be used as the display device 3 for displaying an observation image and the display device 3 for displaying a photographed image. Besides, when similar photographing is performed by illuminating the subject's eye E with infrared light, an infrared photographed image is displayed. An LED may be used as the imaging light source.

A liquid crystal display (LCD) 39 displays a fixation target or a visual target for measuring visual acuity. The fixation target is an indicator for fixating the subject's eye E, and is used when performing fundus photography and OCT measurement.

Part of the light output from the LCD 39 is reflected by the half mirror 33A, is reflected by the mirror 32, travels through the focusing lens 31 and the dichroic mirror 55, passes through the aperture part of the aperture mirror 21, penetrates the dichroic mirror 46, and is refracted by the objective lens 22, thereby being projected onto the fundus Ef. By changing the display position of the fixation target on the screen of the LCD 39, the fixation position of the subject's eye E can be changed.

Further, as with conventional fundus cameras, the fundus camera unit 2 is provided with an alignment optical system 50 and a focus optical system 60. The alignment optical system 50 generates an indicator (an alignment indicator) for the position matching (the alignment) of the optical system with respect to the subject's eye E. The focus optical system 60 generates an indicator (a split indicator) for adjusting the focus with respect to the subject's eye E.

The light (alignment light) output from an LED 51 of the alignment optical system 50 travels through diaphragms 52 and 53 and a relay lens 54, is reflected by the dichroic mirror 55, passes through the aperture part of the aperture mirror 21, penetrates the dichroic mirror 46, and is projected onto the cornea of the subject's eye E by the objective lens 22.

Cornea reflection light of the alignment light travels through the objective lens 22, the dichroic mirror 46 and the abovementioned aperture part. Part of the cornea reflection light penetrates the dichroic mirror 55, passes through the focusing lens 31, is reflected by the mirror 32, penetrates the half mirror 33A, is reflected by the dichroic mirror 33, and is projected onto the light receiving surface of the CCD image sensor 35 by the condenser lens 34. A light receiving image (an alignment indicator) captured by the CCD image sensor 35 is displayed on the display device 3 together with the observation image. A user conducts alignment by the same operation as performed on a conventional fundus camera. Instead, alignment may be performed in such a way that the arithmetic and control unit 200 analyzes the position of the alignment indicator and moves the optical system (automatic alignment).

To conduct focus adjustment, a reflective surface of a reflection rod 67 is arranged in a slanted position on an optical path of the illumination optical system 10. The light (focus light) output from an LED 61 of the focus optical system 60 passes through a relay lens 62, is split into two light beams by a split indicator plate 63, passes through a two-hole diaphragm 64, is reflected by a mirror 65, and is reflected after an image is once formed on the reflective surface of the reflection rod 67 by a condenser lens 66. Further, the focus light travels through the relay lens 20, is reflected by the aperture mirror 21, penetrates the dichroic mirror 46, and is refracted by the objective lens 22, thereby being projected onto the fundus Ef.

Fundus reflection light of the focus light passes through the same route as the cornea reflection light and is detected by the CCD image sensor 35. The display device 3 displays the light receiving image (split indicator) captured by the CCD image sensor 35 together with the observation image. As in the conventional case, the arithmetic and control unit 200 analyzes the position of the split indicator, and moves the focusing lens 31 and the focus optical system 60 for focusing (automatic focusing). Alternatively, the user may perform the focusing manually while visually checking the split indicator.

The dichroic mirror 46 branches an optical path for OCT from an optical path for fundus photography. The dichroic mirror 46 reflects light of wavelength band used in OCT, and transmits light for fundus photography. The optical path for OCT is provided with, in order from the OCT unit 100 side, a collimator lens unit 40, an optical-path-length changing unit 41, an optical scanner 42, a focusing lens 43, a mirror 44, and a relay lens 45.

The optical-path-length changing unit 41 is movable in directions indicated by the arrow in FIG. 1, thereby changing the optical length of the optical path for OCT. This change in the optical path length is used for correcting the optical path length according to the axial length of the subject's eye E, adjusting the interference state, and the like. The optical-path-length changing unit 41 includes, for example, a corner cube and a mechanism for moving the corner cube.

The optical scanner 42 is disposed at a position optically conjugate with the pupil of the subject's eye E. The optical scanner 42 changes the traveling direction of the light (measurement light LS) passing through the OCT optical path. Thereby, the subject's eye E can be scanned with the measurement light LS. The optical scanner 42 includes, for example, a galvano mirror that deflects the measurement light LS in the x direction, a galvano mirror that deflects the measurement light LS in the y direction, and a mechanism(s) that independently drives the galvano mirrors. Thereby, it is possible to scan the measurement light LS in an arbitrary direction in the xy plane.

[OCT Unit]

Figure 2:
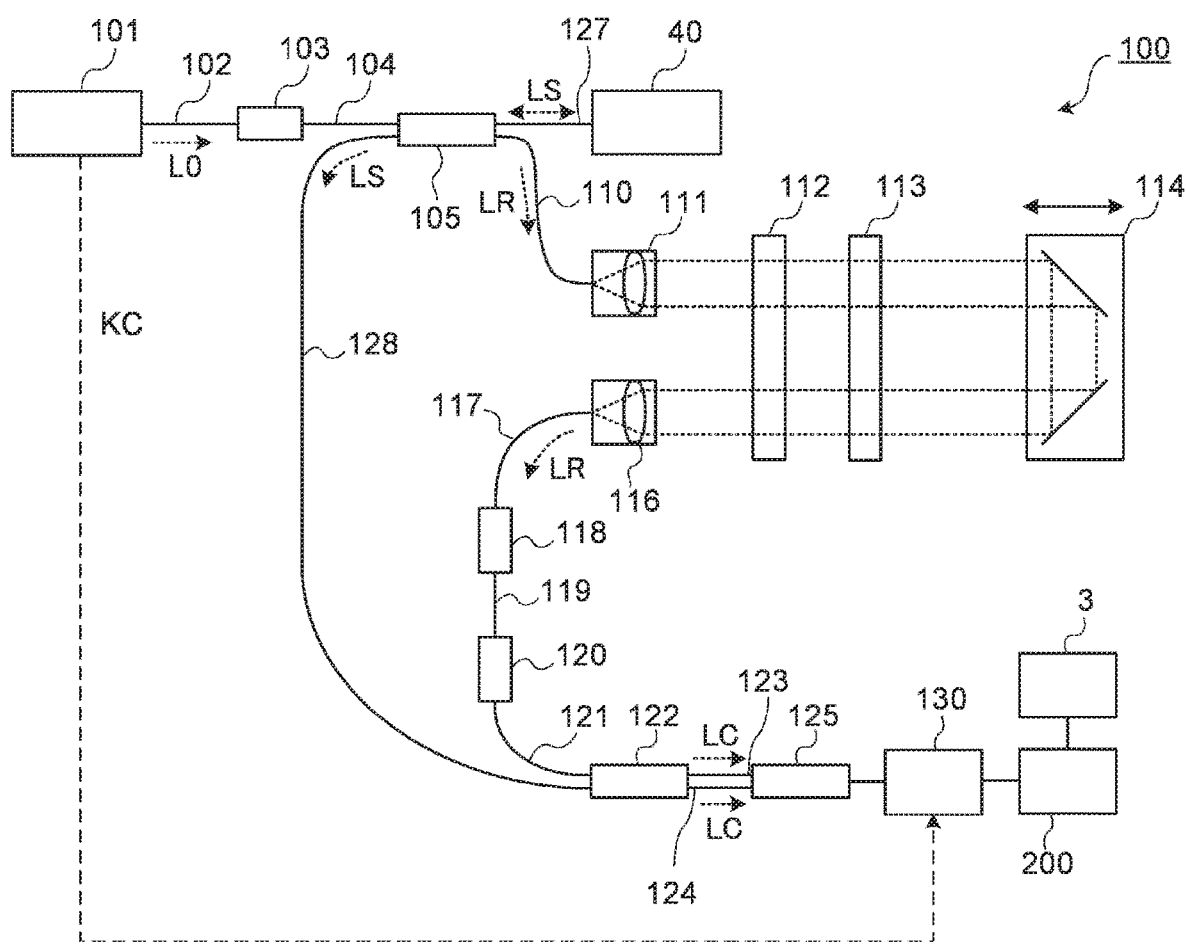
FIG. 2 is a schematic diagram illustrating an example of the configuration of the ophthalmological imaging device of the embodiments.

Exemplary configuration of the OCT unit 100 is shown in FIG. 2. The OCT unit 100 is provided with an optical system for acquiring OCT images of the subject's eye E. The optical system has a similar configuration to a conventional swept-source-type OCT apparatus. That is, the optical system is an interference optical system that splits the light from the wavelength tunable type (wavelength scanning type) light source into the measurement light and a reference light, makes the measurement light returning from the subject's eye E and the reference light having traveled through a reference optical path interfere with each other to generate interference light, and to detect the interference light. The detection result (detection signal) of the interference light obtained by the interference optical system is a signal indicating a spectrum of the interference light, and is sent to the arithmetic and control unit 200.

Like general swept-source-type OCT apparatuses, the light source unit 101 includes a wavelength tunable type (a wavelength scanning type) light source capable of sweeping (scanning) the wavelengths of emitted light. The wavelength tunable type light source includes a laser light source that includes a resonator. The light source unit 101 temporally changes the output wavelengths within the near infrared wavelength bands that cannot be visually recognized with human eyes.

The light L0 output from the light source unit 101 is guided to a polarization controller 103 through an optical fiber 102 and the polarization state thereof is adjusted. The polarization controller 103, for example, applies external stress to the looped optical fiber 102 to thereby adjust the polarization state of the light L0 guided through the optical fiber 102.

The light L0 whose polarization state has been adjusted by the polarization controller 103 is guided to a fiber coupler 105 through an optical fiber 104 and is split into the measurement light LS and the reference light LR.

The reference light LR is guided to a collimator 111 through an optical fiber 110 and becomes a parallel light beam. The reference light LR, which has become the parallel light beam, is guided to the corner cube 114 via the optical path length correction member 112 and the dispersion compensation member 113. The optical path length correction member 112 functions as a delay means to match the optical path length (optical distance) of the reference light LR and the optical path length of the measurement light LS. The dispersion compensation member 113 functions as a dispersion compensating means to match the dispersion characteristics of the reference light LR and the measurement light LS.

The corner cube 114 changes the traveling direction of the reference light LR that has become a parallel light beam by the collimator 111 in the opposite direction. The optical path of the reference light LR incident on the corner cube 114 and the optical path of the reference light LR emitted from the corner cube 114 are parallel. Further, the corner cube 114 is movable in a direction along the incident light path and the emitting light path of the reference light LR. Through this movement, the length of the optical path of the reference light LR is changed.

The configuration shown in FIG. 1 and FIG. 2 include both the optical-path-length changing unit 41 that changes the length of the optical path (measurement optical path, measurement arm) of the measurement light LS and the corner cube 114 that changes the length of the optical path (reference optical path, reference arm) of the reference light LR. However, the ophthalmological imaging device may include any one of the optical-path-length changing unit 41 and the corner cube 114. The ophthalmological imaging device can also change the difference between the measurement optical path length and the reference optical path length by using other optical members.

The reference light LR that has been reflected by the corner cube 114 travels through the dispersion compensation member 113 and the optical path length correction member 112, and is converted from the parallel light flux into a converging light flux by a collimator 116, and enters an optical fiber 117. The reference light LR is guided to a polarization controller 118, and thereby its polarization state is adjusted.

The polarization controller 118 has the same configuration as, for example, the polarization controller 103. The reference light LR whose polarization state has been adjusted by the polarization controller 118 is guided to an attenuator 120 through an optical fiber 119 and the light amount is adjusted under the control of the arithmetic and control unit 200. The reference light LR whose light amount is adjusted by the attenuator 120 is guided to a fiber coupler 122 through an optical fiber 121.

Meanwhile, the measurement light LS generated by the fiber coupler 105 is guided through an optical fiber 127, and is made into a parallel light beam by the collimator lens unit 40. The measurement light LS made into a parallel light beam reaches the dichroic mirror 46 via the optical-path-length changing unit 41, the optical scanner 42, the focusing lens 43, the mirror 44, and the relay lens 45. Then, the measurement light LS is reflected by the dichroic mirror 46, refracted by the objective lens 22, and irradiated onto the subject's eye E. The measurement light LS is scattered (and reflected) at various depth positions of the subject's eye E.

The returning light of the measurement light LS including such backscattered light advances through the same path as the outward path in the opposite direction and is guided to the fiber coupler 105, and then reaches the fiber coupler 122 through an optical fiber 128.

The fiber coupler 122 combines (interferes) the measurement light LS incident through the optical fiber 128 and the reference light LR incident through the optical fiber 121 to generate interference light. The fiber coupler 122 generates a pair of interference light LC by splitting the interference light generated from the measurement light LS and the reference light LR at a predetermined splitting ratio (for example, 1:1). The pair of the interference light LC emitted from the fiber coupler 122 are guided to a detector 125 through optical fibers 123 and 124, respectively.

The detector 125 is, for example, a balanced photodiode that includes a pair of photodetectors for respectively detecting the pair of the interference light LC and outputs the difference between the pair of detection results obtained by the pair of photodetectors. The detector 125 sends the detection result (detection signal) to a DAQ (data acquisition system) 130. A clock KC is supplied from the light source unit 101 to the DAQ 130. The clock KC is generated in the light source unit 101 in synchronization with the output timing of each wavelength sweeping (scanning) within a predetermined wavelength range performed by the wavelength tunable type light source. For example, the light source unit 101 optically delays one of the two pieces of branched light obtained by branching the light L0 of each output wavelength, and then generates the clock KC based on the result of the detection of the combined light of the two pieces of branched light. The DAQ 130 performs the sampling of the detection result obtained by the detector 125 based on the clock KC. The DAQ 130 sends the result of the sampling of the detection result obtained by the detector 125 to the arithmetic and control unit 200. For example, the arithmetic and control unit 200 performs the Fourier transform etc. on the spectral distribution based on the detection result obtained by the detector 125 for each series of wavelength scanning (i.e., for each A line). With this, the reflection intensity profile for each A line is formed. In addition, the arithmetic and control unit 200 forms image data by applying imaging processing to the reflection intensity profiles of the respective A lines.

[Arithmetic and Control Unit]

The configuration of the arithmetic and control unit 200 will be described. The arithmetic and control unit 200 analyzes a detection signal input from the detector 125 to form an OCT image of the subject's eye E. The arithmetic processing for the OCT image formation is performed in the same manner as in the conventional swept-source-type OCT apparatus.

Further, the arithmetic and control unit 200 controls the fundus camera unit 2, the display device 3, and the OCT unit 100. For example, the arithmetic and control unit 200 controls the display device 3 to display the OCT image of the subject's eye E.

The arithmetic and control unit 200 includes a processor, a random access memory (RAM), a read only memory (ROM), a hard disk drive, a communication interface, and the like. In addition, the arithmetic and control unit 200 may include an operation device (input device) such as a keyboard and a mouse, and a display device such as an LCD. The processor is implemented by a circuit(s) such as, for example, a CPU (central processing unit), a GPU (graphics processing unit), an ASIC (application specific integrated circuit), and a PLD (programmable logic device). Examples of PLD include a simple programmable logic device (SPLD), a complex programmable logic device (CPLD), and a field programmable gate array (FPGA). A storage device such as the hard disk drive stores a computer program for controlling the ophthalmological imaging device 1. For example, the arithmetic and control unit 200 reads a program stored in a memory circuit or a storage device and executes it, thereby implementing the functions according to the embodiments.

[Control System]

Figure 3:
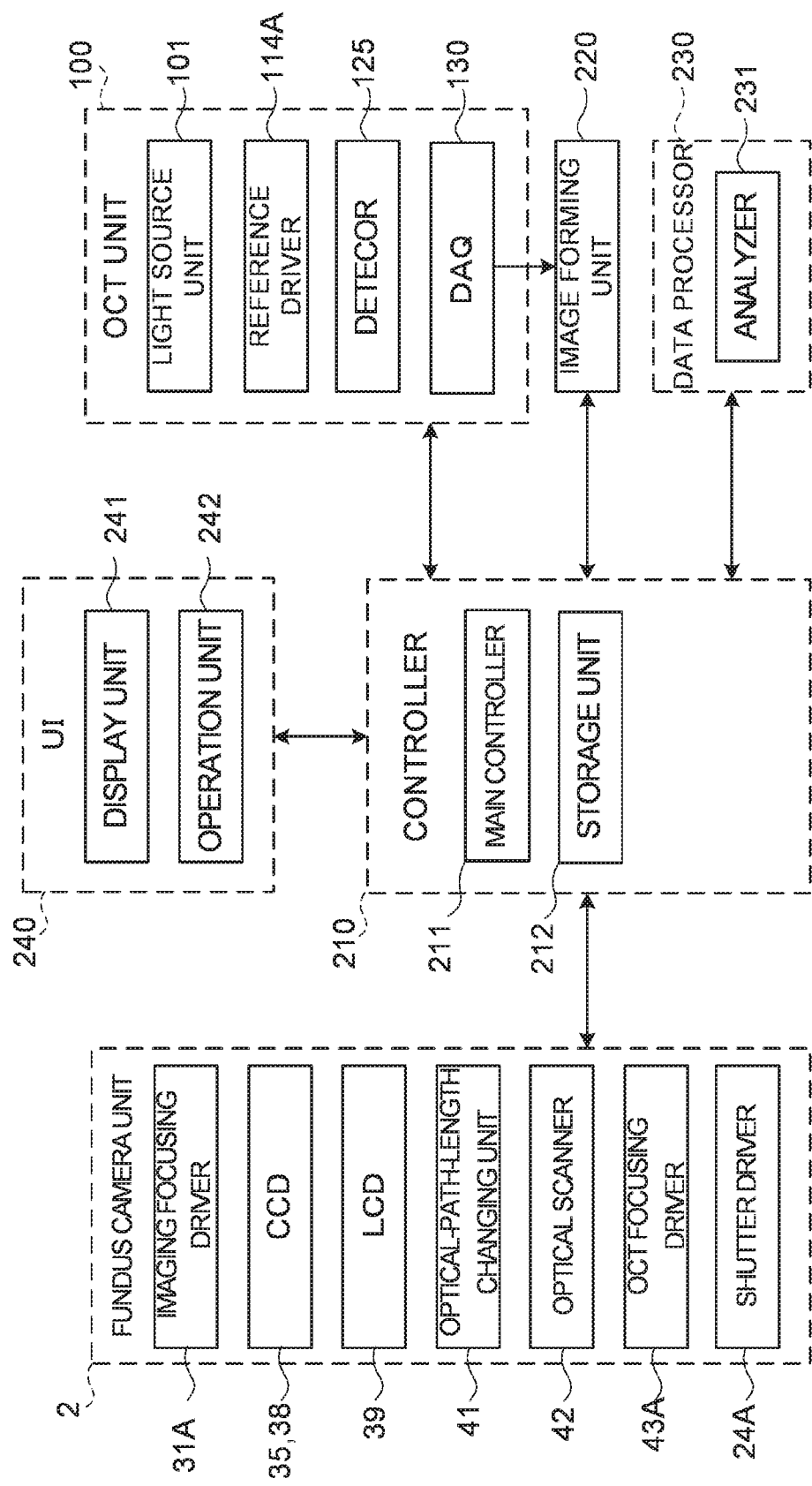
FIG. 3 is a schematic diagram illustrating an example of the configuration of the ophthalmological imaging device of the embodiments.

The configuration of the control system of the ophthalmological imaging device 1 will be described with referring to FIG. 3. In FIG. 3, some components of the ophthalmological imaging device 1 are omitted, and particularly necessary components are selectively shown for describing the present embodiment.

(Controller)

The controller 210 is the center of the control system of the ophthalmological imaging device 1. The controller 210 includes, for example, the aforementioned processor, RAM, ROM, hard disk drive, communication interface, and the like. The controller 210 is provided with a main controller 211 and a storage unit 212.

(Main Controller)

The main controller 211 performs the various kinds of controls described above. In particular, as shown in FIG. 3, the main controller 211 controls an imaging focusing driver 31A, the CCD image sensors 35 and 38, the LCD 39, the optical-path-length changing unit 41, the optical scanner 42, an OCT focusing driver 43A, a shutter driver 24A, and the like of the fundus camera unit 2. Further, the main controller 211 controls components of the OCT unit 100 such as the light source unit 101, the reference driver 114A, the detector 125, and the DAQ 130.

The imaging focusing driver 31A moves the focusing lens 31 in the optical axis direction. With this, the focus position of the imaging optical system 30 is changed. Incidentally, the main controller 211 may control an optical system driver (not illustrated) to three dimensionally move the optical system provided in the fundus camera unit 2. This control is used in alignment and tracking. Here, tracking is to move the optical system of the device according to the movement of the subject's eye E. To perform tracking, alignment and focusing are performed in advance. The tracking is performed by moving the optical system of the device in real time according to the position and orientation of the subject's eye E based on the moving image obtained by imaging the subject's eye E, thereby maintaining a suitable positional relationship in which alignment and focusing are adjusted.

The OCT focusing driver 43A moves the focusing lens 43 along the optical axis of the measurement optical path. Thereby, the focus position of the measurement light LS is changed. The focus position of the measurement light LS corresponds to the depth position (z position) of the beam waist of the measurement light LS.

The shutter driver 24A moves the shutter 24 to insert it into the measurement optical path or to remove it from the measurement optical path. Thereby, when the shutter 24 is inserted into the measurement optical path, at least measurement light among the light passing through the objective lens 22 and heading to the subject's eye E is absorbed without being reflected by the shutter 24. Further, when the shutter 24 is removed from the measurement optical path, light passing through the objective lens 22 is irradiated onto the subject's eye E.

The reference driver 114A moves the corner cube 114 provided in the reference optical path. Thereby, the length of the reference light path is changed. As described above, the ophthalmological imaging device 1 may include any one of the optical-path-length changing unit 41, and the corner cube 114 and the reference driver 114A.

(Storage Unit)

The storage unit 212 stores various types of data. The data stored in the storage unit 212 is, for example, image data of OCT images, image data of fundus images, image data of OCT images for reference described after, subject's eye information, and the like. The storage unit 212 may store the detection result (the detection signal, the interference signal) of the interference light and the detection result of the interference light for reference. The subject's eye information includes information on the subject such as patient ID and name, and information on the subject's eye such as identification information of the left eye/right eye. In addition, the storage unit 212 stores various types of programs and data to run the ophthalmological imaging device 1.

(Image Forming Unit)

An image forming unit 220 forms image data of a tomographic image of the fundus Ef based on detection signals from the detector 125 (DAQ 130). That is, the image forming unit 220 forms the image data of the subject's eye E based on a detection result of the interference light LC obtained by the interference optical system. As in the conventional swept-source-type OCT, the image formation process includes filtering, fast Fourier transform (FFT), and the like. The image data acquired in this manner is a data set including a group of image data formed by imaging the reflection intensity profiles of a plurality of A lines. Here, the A lines are the paths of the measurement light LS in the subject's eye E.

In addition, the image forming unit 220 can form image data of the subject's eye E based on an analysis result of an analyzer 231 described after.

In order to improve the image quality, it is possible to repeatedly perform scan with the same pattern a plurality of times to collect a plurality of data sets, and to compose (i.e., average) the plurality of data sets.

The image forming unit 220 includes, for example, the circuitry described above. Incidentally, "image data" and an "image" based thereon may be treated in the same way in this specification. Further, a site of the subject's eye E and an image thereof may also be treated in the same way.

(Data Processor)

A data processor 230 performs various types of data processing (image processing) and various types of analysis on an OCT image formed by the image forming unit 220. For example, the data processor 230 performs various correction processes such as brightness correction and dispersion correction of images. The data processor 230 performs various types of image processing and analysis on images (fundus image, anterior segment image, etc.) captured by the fundus camera unit 2.

The data processor 230 includes the analyzer 231. The analyzer 231 can perform analysis processing on the detection result (the detection signal) of the interference light acquired by the OCT measurement and the reference data, in addition to the above analysis processing on the OCT image.

The analyzer 231 eliminates noise components of the detection result or the image based on the detection result, by analyzing the detection result (second detection result) of the interference light acquired by the OCT measurement of the subject's eye E and the reference data (first detection result) acquired separately. The above detection result is acquired by the interference optical system in a state that the shutter 24 has been removed from the measurement optical path. The reference data is acquired as a detection result of the interference light by the interference optical system in a state that the shutter 24 is disposed in the measurement optical path, under the same measurement conditions (imaging conditions) as when the above detection result of the interference light was acquired. The measurement conditions include, for example, the setting state of optical member in the measurement path of the interference optical system. Examples of the setting state of optical member like this includes a position of the focusing lens 43, scan length or scan pattern by the optical scanner 42, a changing state of the optical path length by the optical-path-length changing unit 41 or the corner cube 114, and a polarization state by the polarization controller 103 or 118, and the like.

The position of the artifact and its strength depend on the setting state of the optical member as described above. Thus, common noise components due to the above setting state of the optical member are included in the detection result of the interference light acquired by the OCT measurement and the above reference data. Therefore, in a state where the setting state of the optical member as described above is fixed, the detection result of the interference light obtained by the OCT measurement of the subject's eye E and the above reference data are acquired, and the reference data is deducted (subtracted) from the acquired detection result of the interference light. Thereby, the noise-free detection result of the interference light is obtained. The image in which noise such as artifact or the like is eliminated can be obtained by forming image data based on this detection result of the interference light by the image forming unit 220.

The data processor 230 can form volume data (voxel data) of the subject's eye E by performing known image processing such as interpolation processing for interpolating pixels between cross sectional images. In the case of displaying an image based on the volume data, the data processor 230 performs a rendering process on the volume data so as to form a pseudo three-dimensional image viewed from a specific line-of-sight direction.

The data processor 230 can perform position matching between a fundus image and an OCT image. When the fundus image and the OCT image are obtained in parallel, the position matching between the fundus image and the OCT image, which have been (almost) simultaneously obtained, can be performed using the optical axis of the imaging optical system 30 as a reference. Such position matching can be achieved since the optical system for the fundus image and that for the OCT image are coaxial. Besides, regardless of the timing of obtaining the fundus image and that of the OCT image, the position matching between the fundus image and the OCT image can be achieved by performing the position matching between the fundus image with a front image formed by projecting at least part of the image area in the OCT image corresponding to the fundus Ef onto the xy plane. This position matching method can also be employed when the optical system for acquiring fundus image and the optical system for OCT are not coaxial. Further, when both the optical systems are not coaxial, if the relative positional relationship between these optical systems is known, the position matching can be performed with referring to the relative positional relationship in a manner similar to the case of coaxial optical systems.

The data processor 230 that functions as above includes, for example, a processor, a RAM, a ROM, a hard disk drive, a circuit board, and the like. In a storage device such as the hard disk drive, a computer program for causing the processor to execute the functions described above is stored in advance.

(User Interface)

A user interface 240 includes a display unit 241 and an operation unit 242. The display unit 241 includes the aforementioned display device of the arithmetic and control unit 200 and the display device 3. The operation unit 242 includes the aforementioned operation device of the arithmetic and control unit 200. The operation unit 242 may include various kinds of buttons and keys provided on the housing of the ophthalmological imaging device 1, or provided outside the ophthalmological imaging device 1. Further, the display unit 241 may include various kinds of display devices, such as a touch panel placed on the housing of the fundus camera unit 2.

Note that the display unit 241 and the operation unit 242 need not necessarily be formed as separate devices. For example, a device like a touch panel, which has a display function integrated with an operation function, can be used. In such a case, the operation unit 242 includes the touch panel and a computer program. The content of an operation performed using the operation unit 242 is fed to the controller 210 as an electrical signal. Moreover, operations and inputs of information may be performed using a graphical user interface (GUI) displayed on the display unit 241 and the operation unit 242.

The combination of the OCT unit 100, the collimator lens unit 40, the optical-path-length changing unit 41, the optical scanner 42, the focusing lens 43, the mirror 44 and the relay lens 45 is an example of the "interference optical system" according to the embodiments. The shutter 24 is an example of the "optical member" according to the embodiments.

Operation Example

The operation of the ophthalmological imaging device 1 will be described.

Figure 4:
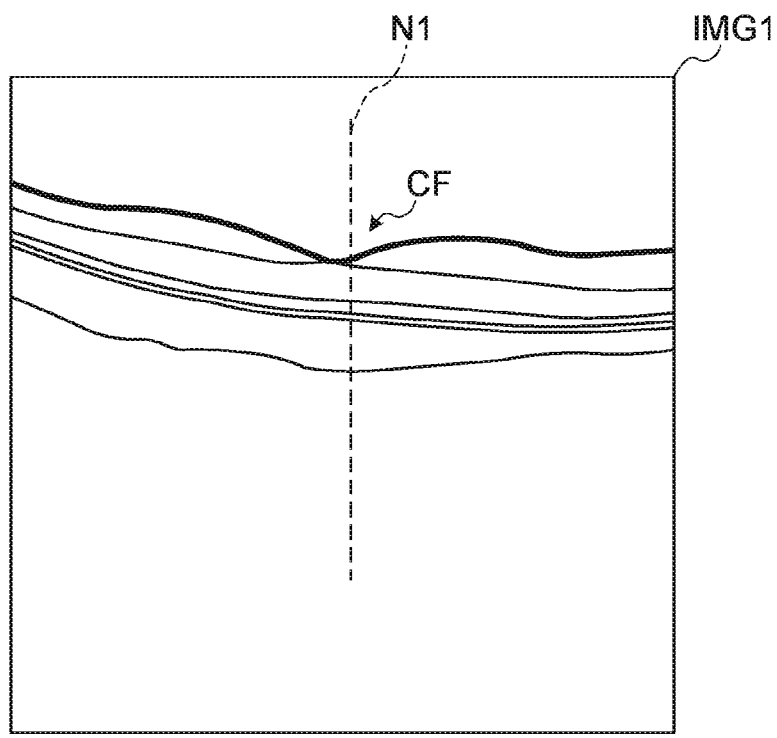
FIG. 4 is a schematic diagram for describing the operation of the ophthalmological imaging device according to a comparative example of the embodiments.

FIG. 4 shows a diagram of a comparative example of the embodiments. FIG. 4 schematically illustrates an OCT image captured by an ophthalmological imaging device of the comparative example.

In the ophthalmological imaging device according to the comparative example, the center of the polarization control (the origin of the scanner coordinate system) of the measurement light by the optical scanner 42 is provided so as to coincide with an optical axis of the objective lens 22. Such position adjustment is performed at the design stage, the shipping process, or the maintenance process. Thereby, in the ophthalmological imaging device according to the present comparative example, the alignment is performed so that an attention site of the subject's eye E is disposed at the position of the optical axis of the objective lens 22. Therefore, the frequency of photographing by scanning including the optical axis becomes high.

However, as shown in FIG. 4, reflection light from a vertex of a lens surface of the objective lens 22 may appear as an artifact N1 in the OCT image IMG1 acquired by scanning including the optical axis of the objective lens 22. For example, despite photographing for the purpose of observing a tomographic image with the fovea centralis CF as the attention site as shown in FIG. 4, the artifact N1 appears near the attention site, thereby it becomes difficult to observe near the attention site in the image. This phenomenon, i.e. artifacts due to the reflection from the optical system provided in the ophthalmological imaging device, is more likely to appear in the OCT image as coherence length becomes longer.

Therefore, in the embodiments, as described above, the noise components of the detection result or the image based on the detection result can be eliminated by analyzing the detection result of the interference light acquired by the OCT measurement and the reference data acquired separately. Thereby, an OCT image in which noises such as artifacts due to the coherence revival phenomenon as well as the reflection from the optical system are disappeared can be obtained. In particular, it becomes possible to observe near the attention site in detail in the OCT images (OCT images obtained by scanning including the optical axis of the objective lens 22) which the frequency of photographing is high.

Figure 5:
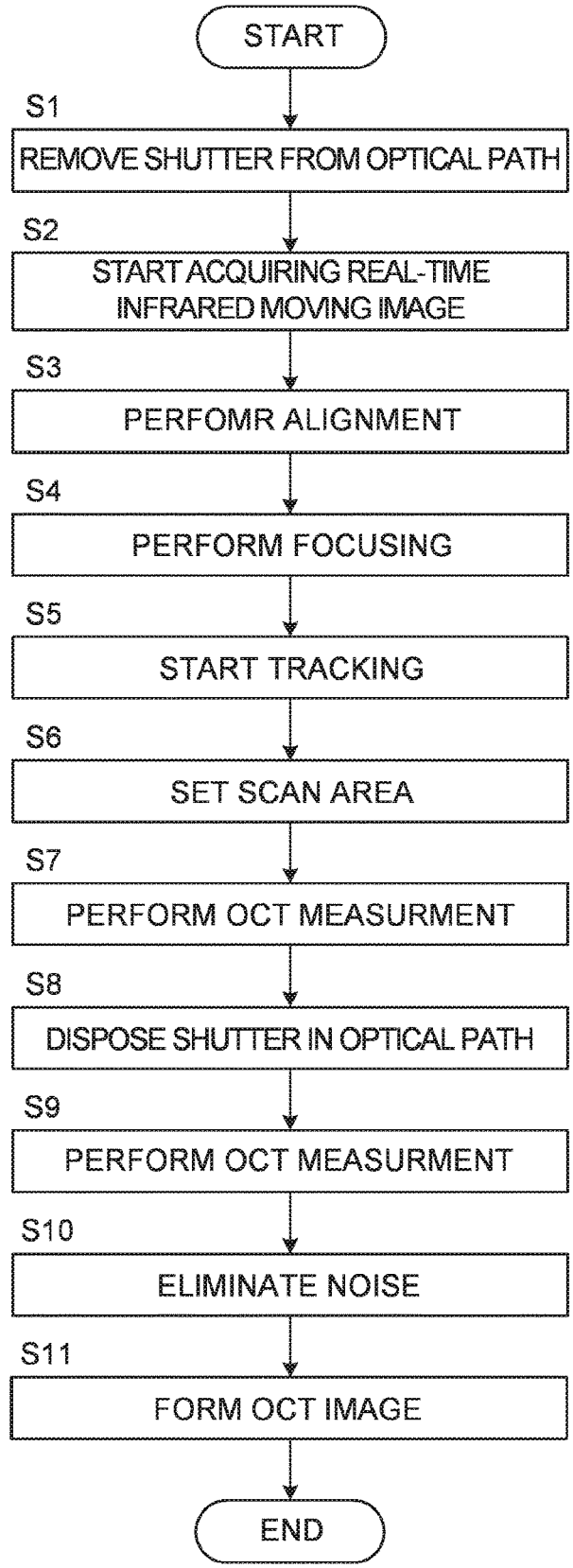
FIG. 5 is a flowchart illustrating an example of the operation of the ophthalmological imaging device according to the embodiments.

FIG. 5 illustrates an example of the operation of the ophthalmologic imaging device 1. This operation example includes position matching between the subject's eye E and the optical system of the device based on an image and setting of a scan area based on an image. The position matching includes alignment (automatic alignment), focusing (automatic focusing), and tracking (automatic tracking) for OCT measurement.

(S1)

First, the main controller 211 controls the shutter driver 24A to remove the shutter 24 from the measurement optical path.

(S2)

Next, the fundus Ef is continuously irradiated with the illumination light from the observation light source 11 (near-infrared light through the action of the visible cut filter 14), thereby starting the acquisition of a near-infrared moving image of the subject's eye E. The near-infrared moving image is acquired in real time until the end of the continuous illumination. The frames of the moving image are temporarily stored in a frame memory (the storage unit 212) and sequentially sent to the data processor 230.

Incidentally, the alignment indicator and the split target are projected onto the subject's eye E respectively by the alignment optical system 50 and the focus optical system 60. Accordingly, the alignment indicator and the split target are represented in the near-infrared moving image. Alignment and focusing can be performed using them. The fixation target is also projected onto the subject's eye E by the LCD 39. The subject is instructed to fixate the eye on the fixation target.

(S3)

The data processor 230 sequentially analyzes the frames of the moving image of the subject's eye E to find the position of the alignment indicator, thereby calculating the movement amount of the optical system. The controller 210 controls the optical system driver (not illustrated) based on the movement amount of the optical system obtained by the data processor 230 to perform automatic alignment.

(S4)

The data processor 230 sequentially analyzes the frames of the moving image of the subject's eye E to find the position of the split target, thereby calculating the movement amount of the focusing lens 31. The controller 210 controls the imaging focusing driver 31A based on the movement amount of the focusing lens 31 obtained by the data processor 230 to perform automatic focusing.

(S5)

Subsequently, the controller 210 starts the control for automatic tracking. Specifically, the data processor 230 analyzes the frames successively acquired by capturing a moving image of the subject's eye E with the optical system in real time, and monitors the movement (positional change) of the subject's eye E. The controller 210 controls the optical system driver (not illustrated) to move the optical system according to the position of the subject's eye E successively obtained. Thereby, the optical system can follow the movement of the subject's eye E in real time. Thus, it is possible to maintain a good positional relationship with proper alignment and focus.

(S6)

The controller 210 displays the near-infrared moving image on the display unit 241 in real time. The user sets a scan area on the near-infrared moving image using the operation unit 242. The scan area may be a one-dimensional region or a two-dimensional region.

If the scan mode of the measurement light LS and an attention site (optic papilla, macula, lesion, etc.) are set in advance, the controller 210 may set the scan area based on the content of the setting. Specifically, the attention site is specified by the image analysis of the data processor 230. Then, the controller 210 can set an area in a predetermined pattern to include the attention site (e.g., such that the attention site is located in the center).

(S7)

The controller 210 controls the light source unit 101 and the optical-path-length changing unit 41 as well as controlling the optical scanner 42 based on the scan area set in S5 to perform OCT measurement of the fundus Ef. The detection results of the interference light acquired by the OCT measurement are stored in the storage unit 212.

(S8)

Next, the main controller 211 controls the shutter driver 24A to insert the shutter 24 into the measurement optical path.

(S9)

Subsequently, the controller 210 preforms the OCT measurement of the fundus Ef under the same measurement conditions as S7. The detection results of the interference light acquired by the OCT measurement are stored in the storage unit 212 as the reference data.

(S10)

The data processor 230 deducts the detection result of the interference light acquired in S9 from the detection result of the interference light acquired in S7 for each A line, in the analyzer 231, thereby new detection results of the interference light are generated. The generated new detection results of the interference light are stored in the storage unit 212.

(S11)

The image forming unit 220 forms a tomographic image of a corresponding A-line based on the new detection results of the interference light stored in the storage unit 212 in S10. If three-dimensional scan is set as the scan mode, the data processor 230 forms a three-dimensional image of the fundus Ef based on a plurality of tomographic images formed by the image forming unit 220. With this, the operation example ends (END).

EXAMPLES OF MODIFICATIONS

First Modification Example

In the aforementioned embodiments, the case has been described in which the detection result of the interference light is the detection signal (the interference signal) of interference light before forming images. However, the configuration of the ophthalmological imaging device according to the embodiments is not limited thereto. For example, the detection result of the interference light may be an image (image data) formed based on the detection result of the interference light.

In this case, the analyzer eliminates noise components of the image based on the detection result of the interference light acquired by the OCT measurement of the subject's eye E, by analyzing the OCT image (second detection result) of the interference light acquired by the OCT measurement of the subject's eye E and the reference image (first detection result) acquired separately. The analyzer forms an image in which noise components are eliminated in pixel unit for example, by performing known subtract processing between images.

Second Modification Example

In the aforementioned embodiments or the first modification example, the case has been described in which the shutter 24 absorbs light which passes through the objective lens 22 and heads toward the subject's eye E. However, the configuration of the ophthalmological imaging device according to the embodiments is not limited thereto. For example, the shutter 24 may reflect (deflect) light which passes through the objective lens 22 and heads toward the subject's eye E in a direction different from the measurement optical path. In the second modification example, a reflecting member may be provided on a surface of the shutter 24 on the objective lens 22 side so as to include an illuminating area of the light heading toward the subject's eye E. As the reflecting member, a member having a low reflectance with respect to the measurement light is used. In this case, an optical element including an absorbing member that absorbs light reflected by the shutter 24 may be provided separately to reduce the influence of reflected light inside the device.

Third Modification Example

In the aforementioned embodiments, the shutter 24 may deflect the light which passes through the objective lens 22 and heads toward the subject's eye E in a direction different from the measurement optical path. That is, in the third modification example, the shutter 24 may include a refractive optical member which refracts the light which passes through the objective lens 22 and heads toward the subject's eye E. In this case, an optical element including an absorbing member that absorbs light refracted by the shutter 24 may be provided separately to reduce the influence of refracted light inside the device.

Fourth Modification Example

In the aforementioned embodiments or their modification examples, the case has been described in which the shutter 24 is inserted into and removed from the measurement optical path between the subject's eye E and the objective lens 22. However, the configuration of the ophthalmological imaging device according to the embodiments is not limited thereto.

Figure 6:
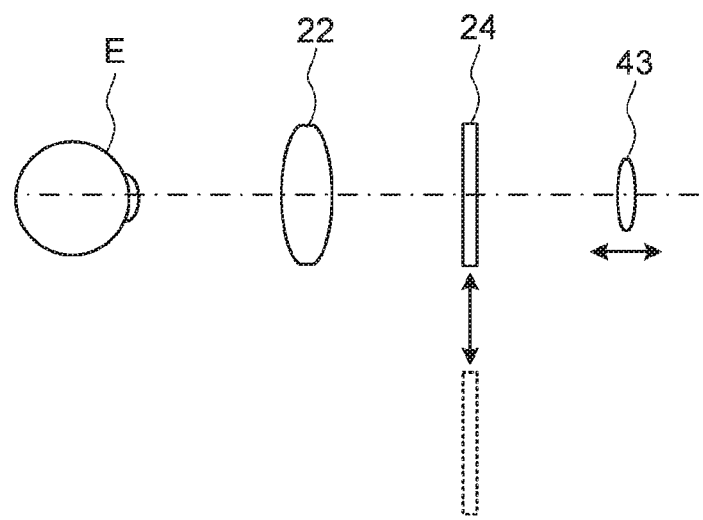
FIG. 6 is a schematic diagram illustrating a principal part of the configuration of an ophthalmological imaging device according to a fourth modification example of the embodiments.

FIG. 6 shows a schematic diagram illustrating a principal part of the configuration of an ophthalmological imaging device according to a fourth modification example of the embodiments. In the fourth modification example, the shutter 24 is inserted into and removed from the measurement optical path between the objective lens 22 and the focusing lens 43. Thereby, noise due to the optical system from the light source side to at least the focusing lens 43 can be eliminated. Further, instead of the position shown in FIG. 6, the shutter 24 may be inserted and removed at an arbitrary position in the measurement optical path.

Fifth Modification Example

Figure 7:
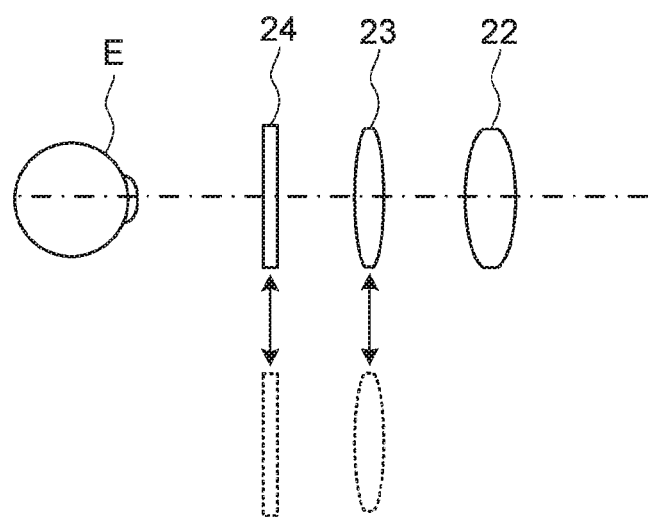
FIG. 7 is a schematic diagram illustrating a principal part of the configuration of an ophthalmological imaging device according to a fifth modification example of the embodiments.

FIG. 7 shows a schematic diagram illustrating a principal part of the configuration of an ophthalmological imaging device according to a fifth modification example of the embodiments. The ophthalmological imaging device according to the fifth modification example includes a front lens 23 capable of being disposed between the objective lens 22 and the subject's eye E. The front lens 23 is capable of being disposed between the objective lens 22 and the subject's eye E manually or automatically. When the front lens 23 is disposed between the objective lens 22 and the subject's eye E, the shutter 24 is capable of being disposed between the front lens 23 and the subject's eye E. Thereby, the image in which noise due to the optical system from the light source side to the front lens 23 is eliminated can be obtained.

Sixth Modification Example

FIG. 8 shows a schematic external view of the ophthalmological imaging device according to a sixth modification example of the embodiments. The ophthalmological imaging device 1 includes a base 300, a stage 310, a head unit 400, a face support 500, and an UI 240. The optical system shown in FIGS. 1 and 2 is provided in the head unit 400. The stage 310 is movable in the front-back direction and in the lateral direction with respect to the base 300. The head unit 400 is formed integrally with the stage 310. The face support 500 is formed integrally with the base 300.

A chin rest 600 and a forehead rest 700 are provided with the face support 500. The face support 500 holds the face of the subject (not shown). For example, the examiner is located opposite the subject with respect to the ophthalmological imaging device 1 while conducting a test. The UI 240 is arranged at the position of the examiner's side. The head unit 400 is movable in the front-back direction and in the lateral direction in accordance with the operation with respect to the UI 240. Further, the head unit 400 is movable in the vertical direction in accordance with the operation with respect to the UI 240. Through these operations, the position of the head unit 400 is adjusted with respect to the face of the subject held by the face support 500. Incidentally, the movement of the head unit 400 in the lateral direction is also performed, for example, to switch a subject's eye tested by the ophthalmological imaging device 1 from the left eye to the right eye or from the right eye to the left eye.

The shutter 24 is provided on the head unit 400 side of the face support 500. The shutter 24 is provided on the head unit 400 side of the chin rest 600 or the forehead rest 700. That is, the shutter 24 is provided on the objective lens side of the face support 500. By relatively moving the base 300 integrally movable with the face support 500 and the head unit 400 accommodating the objective lens 22, the shutter 24 can be inserted into and removed from the optical path of the measurement light which passes through the objective lens 22 accommodated in the head unit 400. The face support 500 is an example of the "support unit" according to the embodiments.

[Effects]

The effects of the ophthalmological imaging device according to the embodiments will be described.

The ophthalmological imaging device according to the embodiments comprises an objective lens (objective lens 22), an interference optical system (the optical system from the OCT unit 100 to the relay lens 45), an image forming unit (image forming unit 220), an optical member (shutter 24), and an analyzer (analyzer 231). The interference optical system divides light (light L0) from a light source (light source unit 101) into measurement light (measurement light LS) and reference light (reference light LR), causes the measurement light to become incident on a subject's eye (subject's eye E) via the objective lens, and detects interference light (interference light LC) between the reference light and return light of the measurement light that has exited from the subject's eye and passed through the objective lens. The image forming unit forms an image of the subject's eye based on a detection result of the interference light which are acquired by the interference optical system. The optical member is capable of being disposed in an optical path of the measurement light, and absorbs the measurement light. The analyzer analyzes a first detection result of the interference light which are acquired by the interference optical system while the optical member is in a state of being disposed in the optical path, and a second detection result of the interference light which are acquired by the interference optical system while the optical member is in a state of having been removed from the optical path, to eliminate noise in the second detection result or in an image based on the second detection result.

The ophthalmological imaging device according to the embodiments comprises an objective lens (objective lens 22), an interference optical system (the optical system from the OCT unit 100 to the relay lens 45), an image forming unit (image forming unit 220), an optical member (shutter 24), and an analyzer (analyzer 231). The interference optical system divides light (light L0) from a light source (light source unit 101) into measurement light (measurement light LS) and reference light (reference light LR), causes the measurement light to become incident on a subject's eye (subject's eye E) via the objective lens, and detects interference light (interference light LC) between the reference light and return light of the measurement light that has exited from the subject's eye and passed through the objective lens. The image forming unit forms an image of the subject's eye based on a detection result of the interference light which are acquired by the interference optical system. The optical member is capable of being disposed in an optical path of the measurement light, and deflects the measurement light in a direction different from the optical path. The analyzer analyzes a first detection result of the interference light which are acquired by the interference optical system while the optical member is in a state of being disposed in the optical path, and a second detection result of the interference light which are acquired by the interference optical system while the optical member is in a state of having been removed from the optical path, to eliminate noise in the second detection result or in an image based on the second detection result.

According to any of the configurations described above, separately from the second detection result of the interference light acquired by irradiating the measurement light on subject's eye by the interference optical system, the first detection result of the interference light which includes noise components due to a state of the interference optical system can be obtained, by insertion and removing of the optical member with respect to the optical path of the measurement light. Thereby, regardless of the state of the interference optical system, the noise of the second detection result or the image based on it can be easily eliminated with a high accuracy by analyzing the first detection result and the second detection result. Thus, an image in which the artifact due to the reflection of the optical system and the phenomenon of coherence revival is eliminated can be obtained, regardless the length of coherence revival or the interval of coherence revival.

Further, in the ophthalmological imaging device according to the embodiments, the optical member may be capable of being disposed between the objective lens and the subject's eye.

According to such a configuration, an image in which noise due to the optical system is eliminated can be obtained with a simple configuration.

Further, in the ophthalmological imaging device according to the embodiments, the optical member may serve as a protective member for the objective lens.

According to such a configuration, the ophthalmological imaging device capable of protecting the objective lens when the device is not in use can be provided.

Further, in the ophthalmological imaging device according to the embodiments, in case that a front lens is disposed between the objective lens and the subject's eye, the optical member may be capable of being disposed between the front lens and the subject's eye.

According to such a configuration, an image in which noise due to the optical system from the light source side to the front lens is eliminated can be obtained, even when the front lens is used.

Further, in the ophthalmological imaging device according to the embodiments, the interference optical system may include a focusing lens (focusing lens 43) disposed in the optical path of the measurement light, and the optical member may be capable of being disposed between the objective lens and the focusing lens.

According to such a configuration, an image in which noise due to the optical system from the light source side to at least the focusing lens is eliminated can be obtained.

Further, the ophthalmological imaging device according to the embodiments may comprise a support unit (face support 500) that support face of the subject, and the optical member may be provided on the objective lens side of the support unit.

According to such a configuration, an image in which noise due to the optical system is eliminated can be obtained, by moving the objective lens and the support unit relatively.

Configurations described above are merely examples for preferably implementing the present invention. Therefore, arbitrary modifications (omission, replacement, addition, etc.) may be applied within the scope of the invention. The configuration to be employed is selected according to the purpose, for example. In addition, depending on the configuration to be employed, actions and effects obvious to those skilled in the art and the actions and the effects described in this specification can be achieved.

In the aforementioned embodiments or their modification examples, a region representing artifact (noise) in the OCT image is specified, reference data regarding partial region including the specified representing region is acquired, and the subtraction of the above detection result regarding at least the representing region may be performed.

In the aforementioned embodiments or their modification examples, the case has been described in which the object to be measured of OCT is the subject's eye (fundus). However, the aforementioned embodiments or their modification examples can be applied to a device that performs OCT on an object to be measured other than the subject's eye. The object to be measured needs not be in vivo site.

The invention claimed is:

1. An ophthalmological imaging device comprising:
an objective lens;
an interference optical system that divides light from a light source into measurement light and reference light, causes the measurement light to become incident on a subject's eye via the objective lens, and detects interference light between the reference light and return light of the measurement light that has exited from the subject's eye and passed through the objective lens;
an image forming unit that forms an image of the subject's eye based on a detection result of the interference light which are acquired by the interference optical system;
an optical member having a surface that includes an absorbing member for absorbing light, the optical member capable of being disposed in an optical path of the measurement light between the objective lens and the subject's eye, for absorbing the measurement light;
an analyzer that analyzes a first detection result of the interference light which are acquired by the interference optical system while the optical member is in a state of being disposed in the optical path, and a second detection result of the interference light which are acquired by the interference optical system while the optical member is in a state of having been removed from the optical path, to eliminate noise in the second detection result or in an image based on the second detection result, wherein the noise in the second detection result or in the image based on the second detection result includes noise components due to a setting state of the optical member on the optical path of the measurement light, the noise components including noise due to reflection from a lens surface of the objective lens; and
a driver that is capable of disposing and removing the optical member in the optical path of the measurement light between the objective lens and the subject's eye.

2. The ophthalmological imaging device of claim 1, wherein the optical member serves as a protective member for the objective lens.

3. The ophthalmological imaging device of claim 1, wherein in case that a front lens is disposed between the objective lens and the subject's eye, the optical member is capable of being disposed between the front lens and the subject's eye.

4. The ophthalmological imaging device of claim 1, wherein the interference optical system includes a focusing lens disposed in the optical path of the measurement light, and the optical member is capable of being disposed between the objective lens and the focusing lens.

5. The ophthalmological imaging device of claim 1, comprising a support unit that supports a face of the subject, wherein the optical member is provided on the objective lens side of the support unit.

6. An ophthalmological imaging device comprising:
an objective lens;
an interference optical system that divides light from a light source into measurement light and reference light, causes the measurement light to become incident on a subject's eye via the objective lens, and detects interference light between the reference light and return light of the measurement light that has exited from the subject's eye and passed through the objective lens;
an image forming unit that forms an image of the subject's eye based on a detection result of the interference light which are acquired by the interference optical system;
an optical member having a surface that includes a reflecting member for reflecting light, the optical member capable of being disposed in an optical path of the measurement light between the objective lens and the subject's eye, for deflecting the measurement light in a direction different from the optical path;
an analyzer that analyzes a first detection result of the interference light which are acquired by the interference optical system while the optical member is in a state of being disposed in the optical path, and a second detection result of the interference light which are acquired by the interference optical system while the optical member is in a state of having been removed from the optical path, to eliminate noise in the second detection result or in an image based on the second detection result, wherein the noise in the second detection result or in the image based on the second detection result includes noise components due to a setting state of the optical member on the optical path of the measurement light, the noise components including noise due to reflection from a lens surface of the objective lens; and
a driver that is capable of disposing and removing the optical member in the optical path of the measurement light between the objective lens and the subject's eye.

7. The ophthalmological imaging device of claim 6, wherein the optical member serves as a protective member for the objective lens.

8. The ophthalmological imaging device of claim 6, wherein in case that a front lens is disposed between the objective lens and the subject's eye, the optical member is capable of being disposed between the front lens and the subject's eye.

9. The ophthalmological imaging device of claim 6, wherein the interference optical system includes a focusing lens disposed in the optical path of the measurement light, and the optical member is capable of being disposed between the objective lens and the focusing lens.

10. The ophthalmological imaging device of claim 6, comprising a support unit that supports a face of the subject, wherein the optical member is provided on the objective lens side of the support unit.

* * * * *